United States Patent
Ueno et al.

(10) Patent No.: US 8,915,119 B2
(45) Date of Patent: Dec. 23, 2014

(54) PARTICULATE MATTER SENSOR, SYSTEM, AND METHOD OF USING A CORRECTION UNIT

(75) Inventors: Tomohiro Ueno, Nagoya (JP); Shigeto Yahata, Obu (JP)

(73) Assignee: Denso Corporation, Kariya (JP)

( * ) Notice: Subject to any disclaimer, the term of this patent is extended or adjusted under 35 U.S.C. 154(b) by 100 days.

(21) Appl. No.: 13/354,644

(22) Filed: Jan. 20, 2012

(65) Prior Publication Data

US 2012/0186330 A1 Jul. 26, 2012

(30) Foreign Application Priority Data

Jan. 20, 2011 (JP) .................................. 2011-009500

(51) Int. Cl.
*G01N 15/06* (2006.01)
*F01N 9/00* (2006.01)

(52) U.S. Cl.
CPC ............ *F01N 9/002* (2013.01); *G01N 15/0656* (2013.01); *F01N 2560/05* (2013.01); *Y02T 10/47* (2013.01)
USPC .......................... 73/23.33; 73/31.02; 73/31.03

(58) Field of Classification Search
USPC .................................. 73/23.33, 31.02, 31.03
See application file for complete search history.

(56) References Cited

U.S. PATENT DOCUMENTS

| | | | |
|---|---|---|---|
| 4,656,832 A | 4/1987 | Yukihisa et al. | |
| 8,176,768 B2 | 5/2012 | Kondo et al. | |
| 8,365,586 B2 * | 2/2013 | Ardanese et al. | ......... 73/114.71 |
| 8,384,397 B2 * | 2/2013 | Bromberg et al. | ............ 324/636 |
| 8,578,756 B2 * | 11/2013 | Suzuki | ......................... 73/28.01 |
| 2001/0035044 A1 * | 11/2001 | Larsson et al. | ............... 73/28.01 |
| 2001/0051108 A1 * | 12/2001 | Schonauer | ................... 422/68.1 |
| 2003/0196499 A1 * | 10/2003 | Bosch et al. | ................. 73/865.5 |
| 2008/0048681 A1 * | 2/2008 | Birkhofer et al. | ............ 324/693 |
| 2008/0264146 A1 * | 10/2008 | Roesch et al. | ............... 73/23.33 |
| 2009/0126458 A1 * | 5/2009 | Fleischer et al. | ............ 73/28.01 |

(Continued)

FOREIGN PATENT DOCUMENTS

DE  10 2006 048 354    4/2008
JP  S59-060018         4/1984

(Continued)

OTHER PUBLICATIONS

Japanese Official Action dated Oct. 31, 2012 issued in corresponding Japanese Application No. 2011-009500, with English translation.

*Primary Examiner* — Lisa Caputo
*Assistant Examiner* — Punam Roy
(74) *Attorney, Agent, or Firm* — Nixon & Vanderhye PC

(57) ABSTRACT

A detection apparatus includes a particulate matter (PM) detection unit, a temperature detection unit, and a correction unit. The PM detection unit includes an insulator, a pair of electrodes, and a detector. The insulator is disposed in an exhaust path of an internal combustion engine through which an exhaust gas flows. The pair of electrodes are arranged in contact with at least a part of the insulator. The detector detects a PM detection value which is a value correlated to an amount of PM in the exhaust gas. The temperature detection unit detects at least one of an exhaust temperature of the exhaust gas passing through the PM detection unit and an insulator temperature of the insulator. The correction unit corrects the PM detection value detected by the PM detection unit based on at least one of the exhaust temperature and the insulator temperature.

21 Claims, 8 Drawing Sheets

(56) References Cited

U.S. PATENT DOCUMENTS

| | | | |
|---|---|---|---|
| 2010/0180668 A1* | 7/2010 | Kruse et al. | 73/28.01 |
| 2010/0312488 A1* | 12/2010 | Diehl et al. | 702/23 |
| 2011/0156727 A1* | 6/2011 | Achhammer et al. | 324/691 |
| 2012/0125081 A1* | 5/2012 | Yadav et al. | 73/23.33 |
| 2012/0159930 A1* | 6/2012 | Snopko et al. | 60/274 |
| 2012/0186230 A1* | 7/2012 | Yahata et al. | 60/274 |
| 2013/0174641 A1* | 7/2013 | Asano et al. | 73/23.31 |
| 2013/0204540 A1* | 8/2013 | Genssle et al. | 702/32 |

FOREIGN PATENT DOCUMENTS

| | | |
|---|---|---|
| JP | S62-035252 | 2/1987 |
| JP | UM-H03-048527 | 10/1991 |
| JP | 2010-032488 | 2/2010 |

\* cited by examiner (INFLUENCE OF THERMAL MIGRATION)

(INFLUENCE ASSOCIATED WITH FLOW SPEED)

1. DEPOSITION ON ELEMENT (INFLUENCE ASSOCIATED WITH FLOW SPEED)

2. SEPARATION FROM ELEMENT

PARTICULATE MATTER SENSOR, SYSTEM, AND METHOD OF USING A CORRECTION UNIT

CROSS-REFERENCE TO RELATED APPLICATION

This application is based on and claims the benefit of priority from earlier Japanese Patent Application No. 2011-009500 filed Jan. 20, 2011, the description of which is incorporated herein by reference.

BACKGROUND OF THE INVENTION

1. Technical Field of the Invention

The present invention relates to a detection apparatus, and in particular to a detection apparatus that detects an amount of particulate matter in an exhaust gas that flows through the exhaust path of an internal combustion engine.

2. Related Art

Recently, internal combustion engines are required to have superior exhaust purification performance. In diesel engines, in particular, removal of so-called exhaust particulates (particulate matter (PM)), such as black smoke, exhausted from the engines is of increasing importance. In order to remove PM, diesel engines are most commonly equipped with a diesel particulate filter (DPF) in the middle of the exhaust pipe.

PM sensors are one of the means for detecting the amount of PM in an exhaust gas. For example, using a detection value derived from a PM sensor disposed downstream of a DPF, a fault of the DPF, if any, can be detected. Further, when such a PM sensor is disposed upstream of a DPF, the amount of PM accumulated in the DPF can be estimated from a detection value derived from the PM sensor. For example, JP-A-S59-060018 discloses a system for estimating the amount of PM accumulated in a DPF by disposing a PM sensor in an exhaust pipe.

As a matter of course, a PM sensor is desired to have high accuracy when used for detecting a fault of a DPF or estimating the amount of PM accumulated in the DPF. However, detection values of a PM sensor depend such as on the operating conditions of the engine and thus high accuracy is not ensured in the detection.

As shown in FIG. 3, a PM sensor 5 of a typical structure includes an insulator 50, a pair of electrodes 51 and 52, and a power supply 54. When the PM sensor 5 is disposed in an exhaust pipe through which PM flows, PM is deposited on the insulator 50. Since PM is electrically conductive, accumulation of PM between the electrodes 51 and 52 to the extent of connecting therebetween will create an electrically conductive state across the electrodes. Accordingly, when voltage is applied across the electrodes 51 and 52 by the power supply 54, current passes across the electrodes 51 and 52. As more PM is accumulated between the electrodes 51 and 52, more current passes across the electrodes. Therefore, the amount of PM accumulated on the insulator, and further, the amount of PM in the exhaust pipe is detected (estimated) based on the current passing across the electrodes.

The inventors of the present invention have expertise that detection values of a PM sensor depend such as on the temperature of and around the PM sensor, the exhaust flow rate around the PM sensor and the output of the PM sensor. In a condition where different temperature regions adjacently exist, so-called thermal migration is induced by which particulates in a higher-temperature region migrate toward a lower-temperature region. For example, as shown in FIG. 10, due to the thermal migration coupled with changing temperature distribution around a sensing element (insulator), the amount of PM deposited on the insulator varies and thus the output of the PM sensor varies.

Further, as shown in FIGS. 11A and 11B, when the exhaust flow speed is high, PM is unlikely to be deposited on the insulator, or, once being deposited on the insulator, is very likely to be separated therefrom. Thus, the output of the PM sensor depends on the exhaust flow speed. Separation of PM is considered to be increased as the amount of accumulated PM is increased. Therefore, the output itself of the PM sensor also influences the output of the PM sensor. Further, the inventors of the present invention also have expertise that, as shown in FIG. 12, a PM layer deposited on the surface of an insulator has electrical resistance that changes with the change of the temperature. Accordingly, for example, when the output of a PM sensor is provided in terms of a current, the output of the PM sensor depends on the temperature of the PM layer.

When the amount of PM in an exhaust pipe is desired to be obtained based on the output of a PM sensor, the influence given to the output of the PM sensor such as by the temperature of and around the PM sensor and the temperature of the PM layer is difficult to be eliminated. Thus, a scheme of appropriately correcting a detection value of the amount of PM in an exhaust pipe is desired to be developed so that the influence mentioned above is eliminated.

SUMMARY

The present disclosure has been made in light of the problem set forth above, and provides a detection apparatus which is able to detect the amount of particulate matter (PM) with higher accuracy by correcting a detection value of the amount of PM in an exhaust pipe derived from a PM sensor, based on the temperature of the PM sensor or the temperature and the flow rate of the exhaust gas around the PM sensor, a detection value of PM, and the like.

According to one aspect of the present disclosure, there is provided a detection apparatus comprising: a particulate matter detection unit that includes an insulator that is disposed in an exhaust path of an internal combustion engine through which an exhaust gas flows, a pair of electrodes that are arranged in contact with at least a part of the insulator, and a detector that detects a particulate matter detection value which is a value correlated to an amount of particulate matter in the exhaust gas, the particulate matter attaching to the insulator and enabling current to flow between the pair of electrodes while voltage is applied across the pair of electrodes; a temperature detection unit that detects at least one of an exhaust temperature of the exhaust gas passing through the particulate matter detection unit and an insulator temperature of the insulator; and a correction unit that corrects the particulate matter detection value detected by the particulate matter detection unit based on the at least one of the exhaust temperature and the insulator temperature detected by the temperature detection unit.

Thus, in the detection apparatus of the present disclosure, a pair of electrodes are arranged on an insulator. In this configuration, voltage is applied across the electrodes that have been electrically connected via the particulate matter (PM) deposited on the insulator to obtain a detection value correlated to the amount of PM in the exhaust gas. In obtaining the detection value, a PM detection value is corrected using the exhaust temperature of the exhaust gas passing through the detection unit or the insulator temperature of the insulator. Thus, a PM detection value can be corrected so as to mitigate the influence of thermal migration associated with the temperature of the detection unit or the temperature distribution around the detection unit, or the influence of change of electrical resistance. In this way, a high-accuracy detection apparatus is realized, which is able to detect the amount of PM (hereinafter also referred to as "PM amount") in an exhaust path, without being affected by thermal migration or change of electrical resistance.

The detection apparatus may further comprise an exhaust flow rate detection unit that detects an exhaust flow rate of the exhaust gas passing through the insulator, wherein the correction unit corrects the particulate matter detection value detected by the particulate matter detection unit based on the exhaust flow rate detected by the exhaust flow rate detection unit and the at least one of the exhaust temperature and the insulator temperature detected by the temperature detection unit.

Thus, in the detection apparatus of the present disclosure, a pair of electrodes are arranged on an insulator. In this configuration, voltage is applied across the electrodes that have been electrically connected via the PM deposited on the insulator to obtain a detection value correlated to the amount of PM in the exhaust gas. In obtaining the detection value, a PM detection value is corrected using the exhaust temperature of the exhaust gas passing through the detection unit or the insulator temperature of the insulator, and using an exhaust flow rate. Thus, a PM detection value can be corrected so as to mitigate the influence of thermal migration associated with the temperature of the detection unit or the temperature distribution around the detecting unit, or the influence of change of electrical resistance, or the influence of deposition and separation of PM associated with the exhaust flow rate. In this way, a high-accuracy detection apparatus is realized, which is able to detect a PM amount in an exhaust path, without being affected by thermal migration or change of electrical resistance or tendency of easy deposition and separation of PM.

The detection apparatus may further comprise a separation rate detection unit that detects a separation rate of particulate matter that separates from the insulator to which particulate matter is attached, wherein the correction unit corrects the particulate matter detection value detected by the particulate matter detection unit based on the separation rate of particulate matter detected by the separation rate detection unit, the exhaust flow rate detected by the exhaust flow rate detection unit, and the at least one of the exhaust temperature and the insulator temperature detected by the temperature detection unit.

Thus, in the detection apparatus of the present disclosure, a pair of electrodes are arranged on an insulator. In this configuration, voltage is applied across the electrodes that have been electrically connected via the PM deposited on the insulator to obtain a detection value correlated to the amount of PM in the exhaust gas. In obtaining the detection value, a PM detection value is corrected using the exhaust temperature of the exhaust gas passing through the detection unit or the insulator temperature of the insulator, and using an exhaust flow rate and a separation rate of PM. Thus, a PM detection value can be corrected so as to mitigate the influence of thermal migration associated with the temperature of the detection unit or the temperature distribution around the detection unit, or the influence of change of electrical resistance, or the influence of deposition and separation of PM associated with the exhaust flow rate, or the influence associated with the separation rate of PM deposited on the insulator. In this way, a high-accuracy detection apparatus is realized, which is able to detect a PM amount in an exhaust path, without being affected by thermal migration or change of electrical resistance or tendency of easy deposition and separation of PM.

The correction unit may include a first sub-correction unit that corrects a rate of change of the particulate matter detection value detected by the particulate matter detection unit in such a manner that, as a value obtained by subtracting the exhaust temperature from the insulator temperature becomes larger, the rate of change of the particulate matter detection value is corrected to a value indicating a larger amount of particulate matter.

Thus, as the value obtained by subtracting the exhaust temperature from the insulator temperature becomes larger, the rate of change of a PM detection value is corrected to a value indicating a larger PM amount. Hence, as the value obtained by subtracting the exhaust temperature from the insulator temperature becomes larger, a PM detection value is corrected accordingly for the elimination of the phenomenon of reducing PM deposited on the insulator due to thermal migration. In this way, a PM detection value is corrected so as to mitigate the influence of thermal migration, thereby realizing a high-accuracy detection apparatus.

The correction unit may include a second sub-correction unit that corrects the particulate matter detection value detected by the particulate matter detection unit in such a manner that, as the exhaust temperature or the insulator temperature becomes higher, the particulate matter detection value is corrected to a value indicating a larger amount of particulate matter.

Thus, as the exhaust temperature or the insulator temperature becomes higher, a PM detection value is corrected to a value indicating a larger PM amount. Hence, as the exhaust temperature or the insulator temperature becomes higher, a PM detection value is corrected accordingly for the elimination of the phenomenon of reducing the electrical resistance of the PM layer deposited on the insulator. In this way, a PM detection value is corrected so as to mitigate the influence of change of electrical resistance, thereby realizing a detection apparatus which outputs an accurate detection value reflecting only a PM amount in an exhaust path.

The correction unit may include a third sub-correction unit that corrects a rate of change of the particulate matter detection value detected by the particulate matter detection unit in such a manner that, as the exhaust flow rate detected by the exhaust flow rate detection unit becomes larger, the rate of change of the particulate matter detection value is corrected to a value indicating a larger amount of particulate matter.

Thus, as the exhaust flow rate becomes higher, the rate of change of a PM detection value is corrected to a value indicating a larger PM amount. Thus, as the exhaust flow rate becomes higher, a PM detection value is corrected accordingly for the elimination of the phenomenon of causing less deposition of PM on the insulator and easy separation of the PM from the insulator once deposited thereon. In this way, a PM detection value is corrected so as to mitigate the influence of temporary deposition and subsequent separation of PM, thereby realizing a high-accuracy detection apparatus for detecting a PM amount in an exhaust path.

The correction unit may include a fourth sub-correction unit that corrects the particulate matter detection value detected by the particulate matter detection unit in such a manner that, as the separation rate of particulate matter detected by the separation rate detection unit becomes larger, the particulate matter detection value is corrected to a value indicating a larger amount of particulate matter.

Thus, as the separation rate of the PM detected by the detection unit becomes higher, the PM detection value is corrected to a value indicating a larger PM amount. Thus, a PM detection value is corrected accordingly for the elimination of the phenomenon of reducing PM due to separation. In this way, a PM detection value is corrected so as to mitigate the influence of separation of PM, thereby realizing a high-accuracy detection apparatus for detecting a PM amount in an exhaust path.

The temperature detection unit may include a temperature sensor that is disposed in the exhaust path and measures the exhaust temperature of the exhaust gas flowing in the exhaust path, and a calculation unit that calculates the exhaust temperature of the exhaust gas passing through the particulate matter detection unit based on the exhaust temperature measured by the temperature sensor and the insulator temperature detected by the temperature detection unit.

Thus, the exhaust temperature of the exhaust gas passing through the PM detection unit is calculated based on a detection value derived from the temperature sensor disposed at the exhaust path, an exhaust flow rate and the insulator temperature. Accordingly, accurate exhaust temperature information is obtained without directly detecting the exhaust temperature of the exhaust gas passing through the PM detection unit. In this way, a PM detection value is corrected for the elimination of the influence such as of thermal migration, using the highly accurate temperature information.

The detection apparatus may further comprise a heating unit that includes a resistor and a power unit that supplies the electric power to the resistor to heat the insulator, wherein the temperature detection unit includes a first detection unit that detects the insulator temperature based on a resistance value of the resistor.

Thus, the PM deposited on the insulator is burned by the heating unit to thereby regenerate the PM detection unit. Further, the insulator temperature can also be calculated based on the change of electrical resistance of the heating unit. In this way, the insulator temperature can also be detected using a unit for regenerating the PM detection unit.

The temperature detection unit may include a temperature sensor that that is disposed in the exhaust path and measures the exhaust temperature of the exhaust gas flowing in the exhaust path, an exhaust flow rate detection unit that detects an exhaust flow rate of the exhaust gas passing through the insulator, and a second detection unit that detects the insulator temperature based on the exhaust temperature measured by the temperature sensor and the exhaust flow rate detected by the exhaust flow rate detection unit.

For example, in calculating the insulator temperature by the second detection unit, a formula model based on a physical phenomenon may be used. Thus, the temperature of the element of the PM detection unit can be calculated in a simple configuration of using a formula model, omitting a unit for directly detecting the temperature.

The separation rate detection may include an exhaust flow rate detection unit that detects an exhaust flow rate of the exhaust gas passing through the insulator, and a calculation unit that calculates the separation rate of particulate matter based on the particulate matter detection value and the exhaust flow rate.

Thus, a PM separation rate, which is calculated based on a PM detection value and an exhaust flow rate, exhibits high accuracy. In this way, a detection apparatus is realized, which is able to correct a PM detection value to one having high accuracy, using a highly accurate PM separation rate.

The detection apparatus may further comprise at least one of an instruction unit that instructs a fuel injection quantity for a cylinder of the internal combustion engine, a temperature sensor that that is disposed in the exhaust path and measures the exhaust temperature of the exhaust gas flowing in the exhaust path, and a pressure detection unit that detects an exhaust path pressure in the exhaust path of the internal combustion engine; and an intake volume detection unit that detects an intake volume of an intake gas flowing in an intake path of the internal combustion engine, wherein the exhaust flow rate detection unit detects the exhaust flow rate based on the intake volume detected by the intake volume detection unit and at least one of the fuel injection quantity instructed by the instruction unit, the exhaust temperature measured by the temperature sensor, and the exhaust path pressure detected by the pressure detection unit.

Thus, an exhaust flow rate is calculated based on an intake volume, a fuel injection quantity, the temperature in an exhaust path, and the pressure in the exhaust path of the internal combustion engine. Thus, an exhaust flow rate can be calculated with high accuracy. In this way, a detection apparatus is realized, which is able to correct a PM detection value to one having high accuracy, using a highly accurate exhaust flow rate.

BRIEF DESCRIPTION OF THE DRAWINGS

In the accompanying drawings.

DETAILED DESCRIPTION OF THE PREFERRED EMBODIMENTS

With reference to the accompanying drawings, hereinafter are described some embodiments of the present invention.

(First Embodiment)

Figure 1:
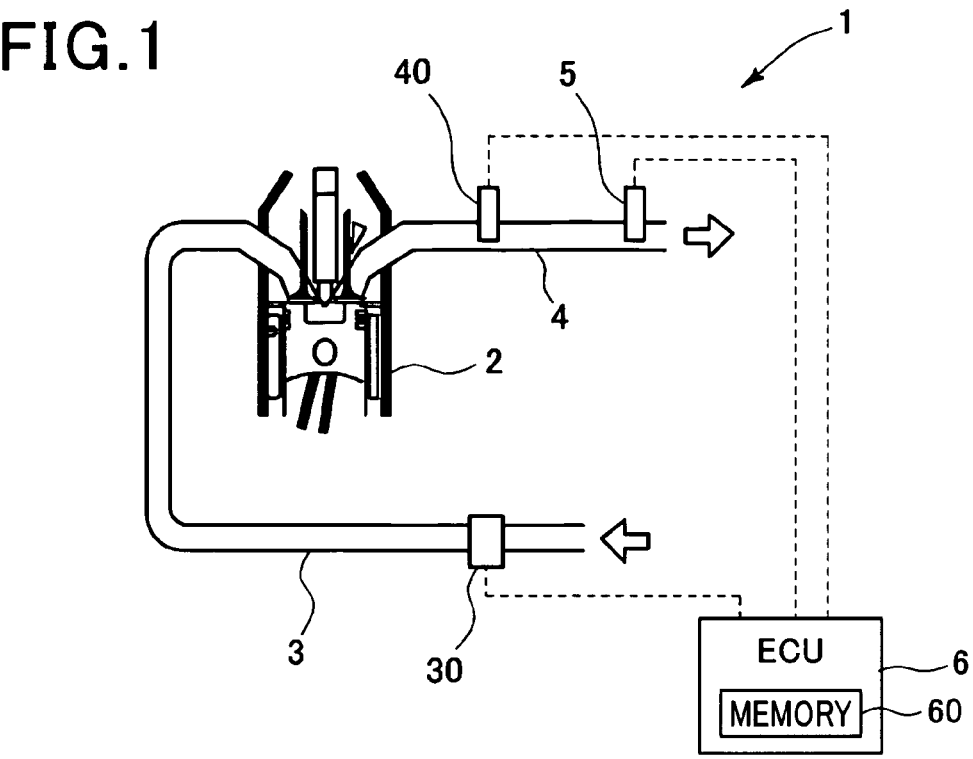
FIG. 1 is a schematic diagram illustrating a detection apparatus according to a first embodiment of the present invention.

Referring first to FIGS. 1 to 4, 7 and 10 to 13, a first embodiment of the present invention is described. FIG. 1 is a schematic diagram illustrating a detection system 1 that configures a detection apparatus according to the first embodiment. The detection system 1 is used for detecting the amount of particulate matter (PM) flowing through an exhaust pipe (exhaust path) 4 (hereinafter this amount is also referred to as "PM amount") of a diesel engine 2 (engine) that is an internal combustion engine. The detection system 1 also includes an intake pipe 3 that supplies intake gas (air) to the engine 2. The intake pipe 3 (intake path) is provided with an air flow meter 30 that detects an intake volume (e.g., mass flow rate per unit time). The exhaust pipe 4 of the engine 2 is provided with an exhaust temperature sensor 40 and a PM sensor 5.

The exhaust temperature sensor 40 detects the temperature of an exhaust gas (hereinafter also referred to as "exhaust temperature"). The PM sensor 5 detects a PM amount in an exhaust gas. The detection system 1 also includes an electronic control unit (ECU) 6 that controls the system 1. The ECU 6 has a configuration similar to that of a normally used computer and includes a CPU (central processing unit) for carrying out several calculations and a memory 60 for storing various pieces of information including various maps to be hereinafter described.

Figure 2A:
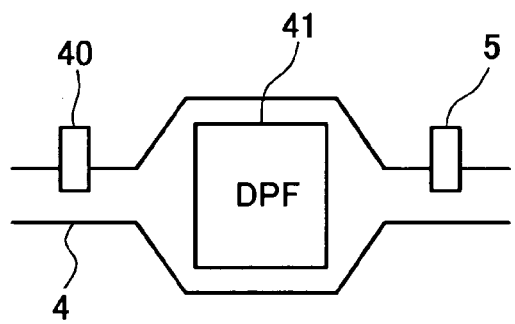
FIGS. 2A and 2B are schematic diagrams each illustrating an example of arranging a diesel particulate filter (DPF), according to the first embodiment.
Figure 2B:
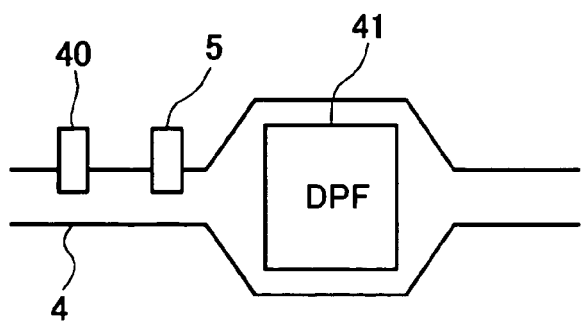

In FIG. 1, a diesel particulate filter (DPF) is omitted. Examples of arrangement in the system 1 including a DPF 41 are shown in FIGS. 2A and 2B. In FIG. 2A, the DPF 41 is arranged between the exhaust temperature sensor 40 and the PM sensor 5. In FIG. 2B, the DPF 41 is arranged downstream of the exhaust temperature sensor 40 and the PM sensor 5. In the example of FIG. 2A, the amount of PM that has passed through the DPF 41 is detected by the PM sensor 5 to thereby enable detection of the occurrence of a fault, if any, in the DPF 41. In the example of FIG. 2B, the amount of PM flowing into the DPF 41 is detected by the PM sensor 5 to thereby enable estimation of the amount of PM accumulated in the DPF 41 (hereinafter this amount is also referred to as "PM accumulation").

Figure 3:
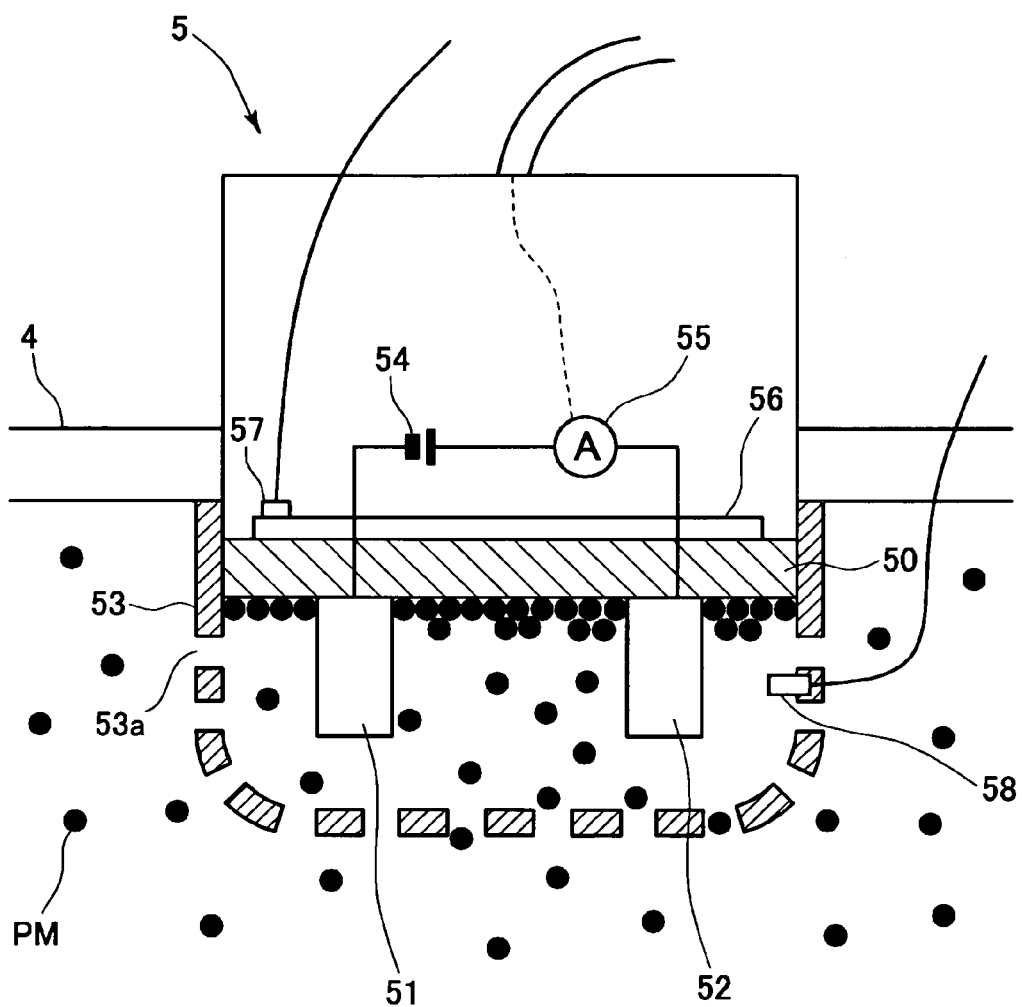
FIG. 3 is a schematic diagram illustrating an example of a structure of a PM sensor, according to the first embodiment.

FIG. 3 shows an example of the structure of the PM sensor 5. The PM sensor 5 includes a plate-shaped sensing element 50, i.e. an insulator, and a pair of electrodes 51 and 52 formed on the sensing element 50. The entirety is covered with a cover 53 made of metal or the like. A number of holes 53a are formed in the cover 53. PM flows into the cover 53 through the holes 53a, PM has viscosity and thus is deposited and accumulated on the sensing element 50. PM also has electrical conductivity. Therefore, when PM is accumulated on the sensing element 50 to the extent of connecting the electrodes 51 and 52, an electrically conductive state is created across the electrodes.

The PM sensor 5 includes a DC power supply 54 and an ammeter 55. The DC power supply 54 applies voltage across the electrodes 51 and 52. When the electrically conductive PM is accumulated on the sensing element 50 and an electrically conductive state is created across the electrodes, current passes across the electrodes 51 and 52. The current is measured by the ammeter 55 and the measured current is outputted as a sensor output to the ECU 6.

The PM sensor 5 also includes a heater 56 and a heater controller 57. For example, the heater 56 may be a metal wire (conductor wire) provided on the rear face of the sensing element 50. Under the control of the heater controller 57, current is passed through the heater 56 to raise the temperature of the heater 56 with its electrical resistance. Thus, the heater 56 burns and removes the PM accumulated on the surface of the sensing element 50. As a result, the PM sensor 5 is regenerated.

The heater controller 57 detects a voltage applied to the heater 56 and a current passing through the heater 56 to obtain an electric resistance of the heater 56 through a division calculation based on the detected voltage and current. As is well known, electrical resistance changes with the change of temperature. Thus, the heater controller 57 is able to detect the temperature of the heater 56, i.e. able to approximately detect the temperature of the sensing element 50. Alternative to this, the heater controller 57 may transmit the detected voltage and current to the ECU 6 so that the ECU 6 can calculate the electrical resistance and the temperature of the heater 56.

Alternatively, a map may be prepared in advance based on exhaust temperature and exhaust flow rate, for the calculation of the temperature of the sensing element 50. The map may be set in advance in the ECU 6 (e.g., the memory 60). The exhaust temperature may be measured using the exhaust temperature sensor 40. The process of calculating the exhaust flow rate will be described later. The PM sensor 5 also includes an exhaust temperature sensor 58 which is used for detecting the temperature inside the cover 53.

As will be described later, in the present embodiment, the temperature inside the cover 53 is detected. Either of the following two processes may be used for the detection. A first process is to directly detect the temperature inside the cover 53 using the exhaust temperature sensor 58. A second process is to estimate the temperature inside the cover 53 using the exhaust temperature sensor 40 and the temperature of the sensing element 50. In the second process, a formula model is prepared in advance for the calculation of the temperature inside the cover 53 based on the detection value derived from the exhaust temperature sensor 40 and the temperature of the sensing element 50. The second process does not require the use of the exhaust temperature sensor 58.

Figure 10:
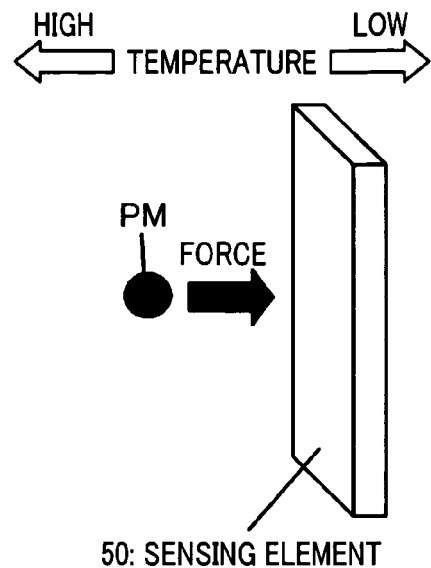
FIG. 10 is a schematic diagram illustrating influence of thermal migration on PM accumulation, according to the first embodiment.

In the configuration described above, the system 1 calculates a value accurately reflecting a PM amount in the exhaust pipe 4, using the output of the PM sensor 5 as a basis. FIGS. 10 to 12 show key points for accurately correcting a PM amount in the exhaust pipe 4.

FIG. 10 shows influence of thermal migration on PM accumulation. Let us assume that, in the exhaust temperature distribution around the sensing element 50, a region farther from the sensing element 50 has a higher temperature and a region nearer to the sensing element 50 has a lower temperature. In this case, due to so-called thermal migration, PM moves from the higher-temperature region to the lower-temperature region, i.e. moves toward the sensing element 50. Let us assume, on the other hand, that the region nearer to the sensing element 50 has a higher temperature and the region farther from the sensing element 50 has a lower temperature. In this case, PM moves away from the sensing element 50 due to thermal migration.

More PM is accumulated on the sensing element 50 in the former case than in the latter case and thus the output of the PM sensor 5 is larger in the former case. Accordingly, the same PM amount in the exhaust pipe 4 will result in different outputs of the PM sensor 5, due to thermal migration coupled with changing temperature distribution in and around the sensing element 50. Therefore, if a value correctly reflecting only the PM amount in the exhaust pipe 4 is desired to be obtained, the influence of thermal migration is required to be eliminated. Specifically, in this case, a rate of change in a PM amount in the exhaust pipe 4 is required to be corrected such that the influence of thermal migration is eliminated.

Figure 11A:
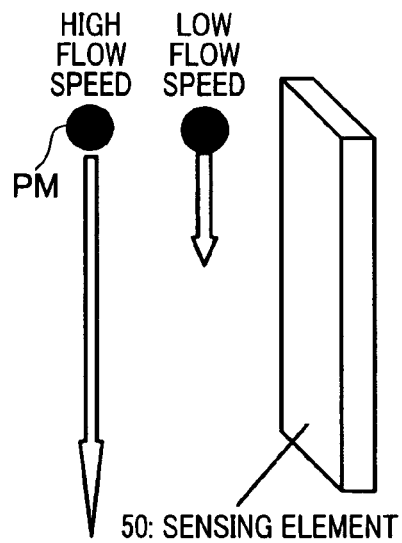
FIGS. 11A and 11B are schematic diagrams each illustrating influence of exhaust flow speed on PM accumulation, according to the first embodiment.
Figure 11B:
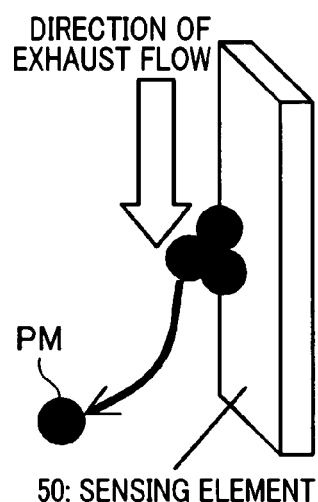
Figure 12:
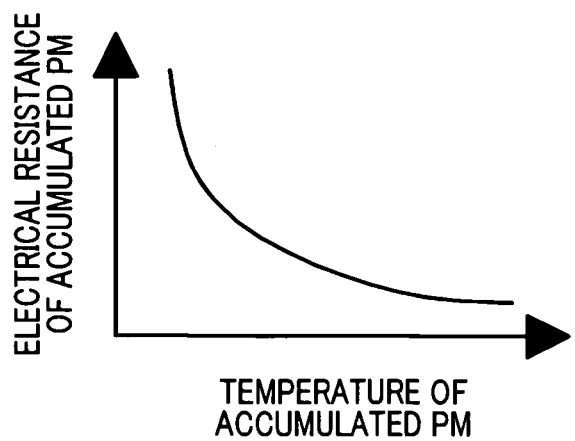
FIG. 12 is a graph illustrating correlation of electrical resistance of accumulated PM, relative to temperature of accumulated PM, according to the first embodiment.

FIGS. 11A and 11B are schematic diagrams each illustrating the influence of flow speed of an exhaust gas (hereinafter referred to as "exhaust flow speed") on PM accumulation. Comparing with low exhaust flow speed, high exhaust flow speed allows more PM to pass by the sensing element 50 of the PM sensor 5 without allowing deposition thereon. In addition, high exhaust flow speed may tend to allow the PM that has once deposited on the sensing element 50 to be separated therefrom. Thus, high exhaust flow speed may have an influence of reducing the output of the PM sensor 5, and thus a correction of eliminating the influence is required to be made.

FIG. 12 is a graph illustrating electrical resistance of an accumulated PM layer. In the graph, the vertical axis indicates electrical resistance across the electrodes 51 and 52 connected via the PM layer accumulated on the sensing element 50. The horizontal axis in the graph indicates the temperature of the PM layer. As shown in FIG. 12, as the temperature increases, the electrical resistance across the electrodes 51 and 52 connected via the PM layer is reduced. The causes of this phenomenon are considered to be as follows.

As the temperature increases, the particulates of PM are oscillated more violently. Accordingly, the particulates will have a larger contact area therebetween. A larger contact area means that a larger area is provided for current when the current passes through contact portions between the particulates. Owing to the large contact area, current easily passes through the PM layer to thereby increase the output of the PM sensor 5. This state is equivalent to the state where the electrical resistance is small. In this way, when a value correctly reflecting a PM amount in the exhaust pipe 4 is desired to be obtained, a PM amount is required to be corrected. Correction of the PM amount can eliminate the influence caused by the change of electrical resistance, which change is caused by the change of temperature.

In the detection system 1, a PM amount in the exhaust pipe 4 is corrected so as to eliminate the influences of the three phenomena (i.e. phenomena associated with thermal migration, exhaust flow speed and electrical resistance of PM layer) described above. The process of elimination is shown in a flow diagram of FIG. 4. The process shown in FIG. 4 (as well as the processes shown in FIGS. 5 and 6 described later) may be programmed and stored in advance in a memory 60, for example, of the ECU 6, for automatic execution of the program by the ECU 6.

Figure 4:
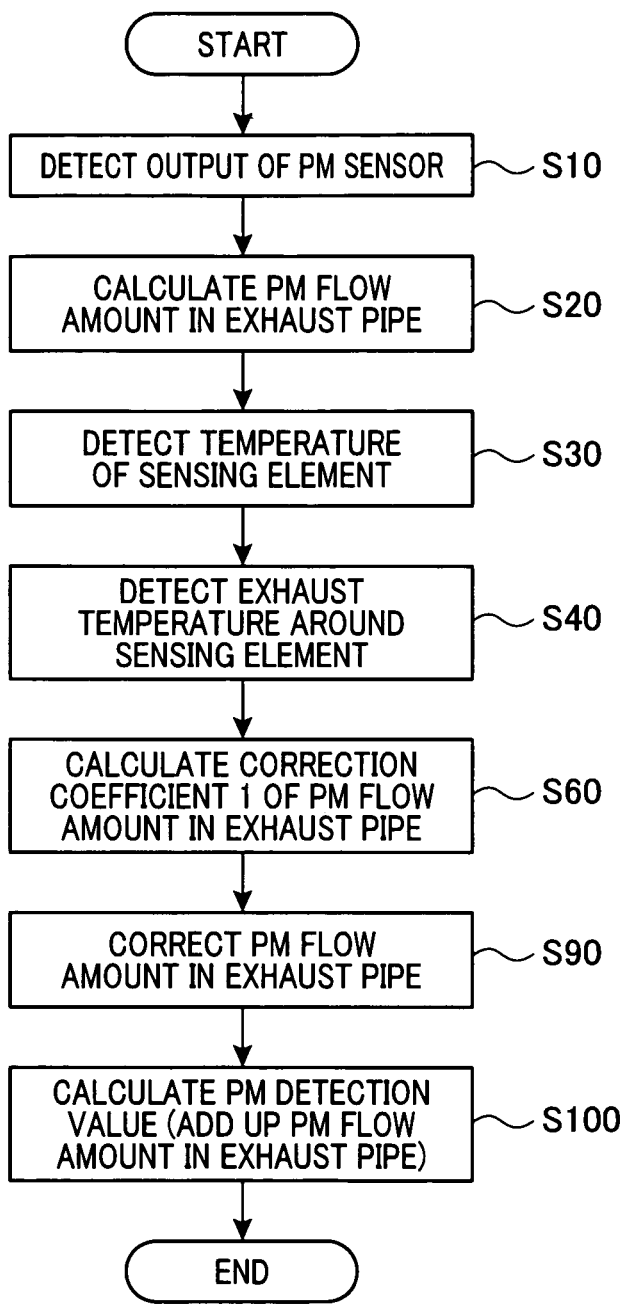
FIG. 4 is a flow diagram illustrating a process performed by the detection apparatus according to the first embodiment.

In the process shown in FIG. 4, at step S10, the ECU 6 acquires an output of the PM sensor 5.

Then, at step S20, the ECU 6 calculates an amount of the PM that has flowed, within a predetermined time, through an arbitrary cross section of the exhaust pipe 4 perpendicular to the axial direction thereof (hereinafter referred to as "PM flow amount in the exhaust pipe 4"). The amount of PM may be calculated by referring to correlation data prepared in advance, in which variation in the detection values of the PM sensor 5 before and after the predetermined time is correlated to PM flow amount in the exhaust pipe 4. Theoretically, when a PM flow amount in the exhaust pipe 4 becomes "a" times larger, variation in the detection values of the PM sensor 5 in a unit time may also become "a" times larger. Thus, variation in the outputs of the PM sensor 5 can be correlated to PM flow amount in the exhaust pipe 4.

Then, at step S30, the ECU 6 acquires a temperature of the sensing element 50. The temperature of the sensing element 50 may be approximately obtained from the temperature of the heater 56 as mentioned above.

Then, at step S40, the ECU 6 acquires an exhaust temperature around the sensing element 50 (or an exhaust temperature inside the cover 53). The exhaust temperature may be acquired using either of the exhaust temperature sensor 58 and the exhaust temperature sensor 40 as mentioned above.

Figure 7:
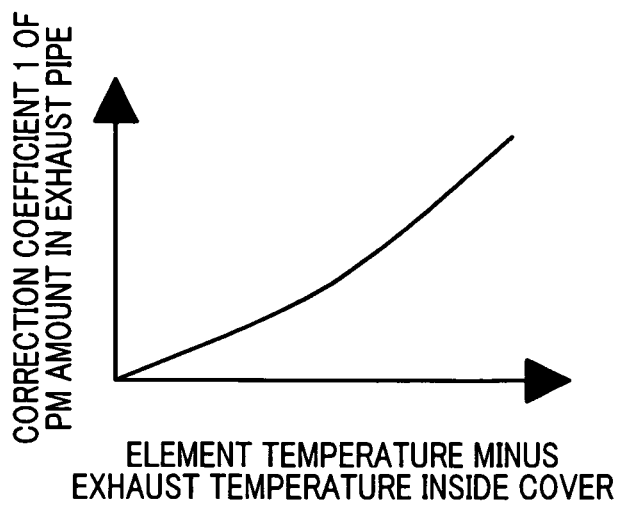
FIG. 7 is a graph illustrating correlation of correction coefficient for PM flow amount in an exhaust pipe, relative to difference between temperature of a sensing element and temperature inside its cover (temperature in a position between the sensing element and its cover), according to the first embodiment.

Subsequently, at step S60, the ECU 6 calculates a correction coefficient 1 for the PM flow amount in the exhaust pipe 4 (hereinafter also referred to as "coefficient 1"). The coefficient 1 (as well as coefficients 2 and 3 described later) is a positive value used for correcting the PM flow amount in the exhaust pipe 4 by, for example, multiplying the PM flow amount in the exhaust pipe 4 with the coefficient 1. In other words, the coefficient 1 is used for correcting the influence of thermal migration described above. For example, the coefficient 1 may be obtained using a map, an example of which is shown in FIG. 7. The map is prepared in advance in the ECU 6 (e.g., the memory 60).

In FIG. 7, the vertical axis indicates the correction coefficient 1 for the PM amount in the exhaust pipe 4. The horizontal axis indicates value obtained by subtracting the exhaust temperature inside the cover 53 from the temperature of the sensing element 50. The temperature of the sensing element 50 is acquired at step S30. The exhaust temperature inside the cover 53 is acquired at step S40. As described above, as the value obtained by subtracting the exhaust temperature inside the cover 53 from the temperature of the element becomes larger, the increase in the output of the PM sensor 5 for the PM flow amount in the exhaust pipe 4 becomes smaller due to being influenced by thermal migration. Accordingly, as the value obtained by subtracting the exhaust temperature inside the cover 53 from the temperature of the element becomes larger, the coefficient 1 is set to a larger (positive) value. The vertical and horizontal axes of FIG. 7 may be calibrated as appropriate according such as to the characteristics of the system to be used.

In thermal migration, as the value obtained by subtracting the exhaust temperature inside the cover 53 from the temperature of the element becomes larger, PM has a higher tendency of moving away from the sensing element 50. In order to eliminate this tendency, the curve plotted in the graph of FIG. 7 for determining the coefficient 1 is protruded downward. In other words, as the value obtained by subtracting the exhaust temperature inside the cover 53 from the temperature of the element becomes larger, the increase rate (the inclination of the curve) of the coefficient 1 is rendered to be higher (steeper). At step S60, the coefficient 1 is calculated using the map shown in the graph of FIG. 7.

Subsequently, at step S90, the PM flow amount in the exhaust pipe 4 is corrected using the correction coefficient 1 calculated at step S60 to obtain a "corrected PM flow amount in the exhaust pipe 4". Specifically, at this step, the PM flow amount in the exhaust pipe 4 calculated at step S20 is multiplied by the coefficient 1 calculated at step S60.

Then, at step S100, the corrected PM flow amount in the exhaust pipe 4 that has been calculated at step S90 is added up. Thus, the total amount of PM that has flowed through the exhaust pipe 4 (PM detection value) is calculated.

The PM detection value calculated at step S100 may be corrected referring to the graph of FIG. 12. As described above, as the temperature of PM accumulated on the surface of the sensing element 50 is increased, the electrical resistance against the current passing between the particulates is decreased. As the electrical resistance is decreased, the output, i.e. the current, of the PM sensor 5 is increased. Accordingly, in order to eliminate the influence of this phenomenon, the PM detection value is corrected so as to be smaller as the PM accumulated on the surface of the sensing element 50 has a higher temperature.

Figure 13:
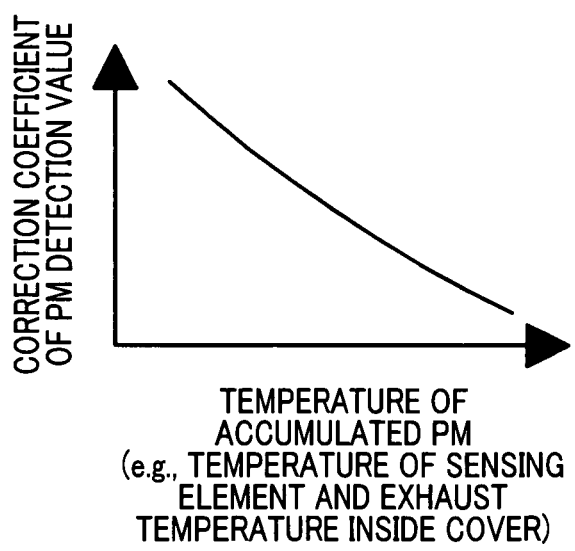
FIG. 13 is a graph illustrating correlation of correction coefficient for PM detection value, relative to temperature of accumulated PM, according to the first embodiment.

The temperature of the PM accumulated on the surface of the sensing element 50 may be approximated such as by the temperature of the sensing element 50 or the temperature inside the cover 53 (or a value intermediate between these two temperatures, e.g., an average value). Thus, the map for calculating a correction coefficient in this case will be as shown in FIG. 13. The map is prepared in advance in the ECU 6 (e.g., the memory 60). The PM detection value can be corrected by, for example, multiplying the PM detection value with a correction value calculated based on the map shown in the graph of FIG. 13.

(Second Embodiment)

Figure 5:
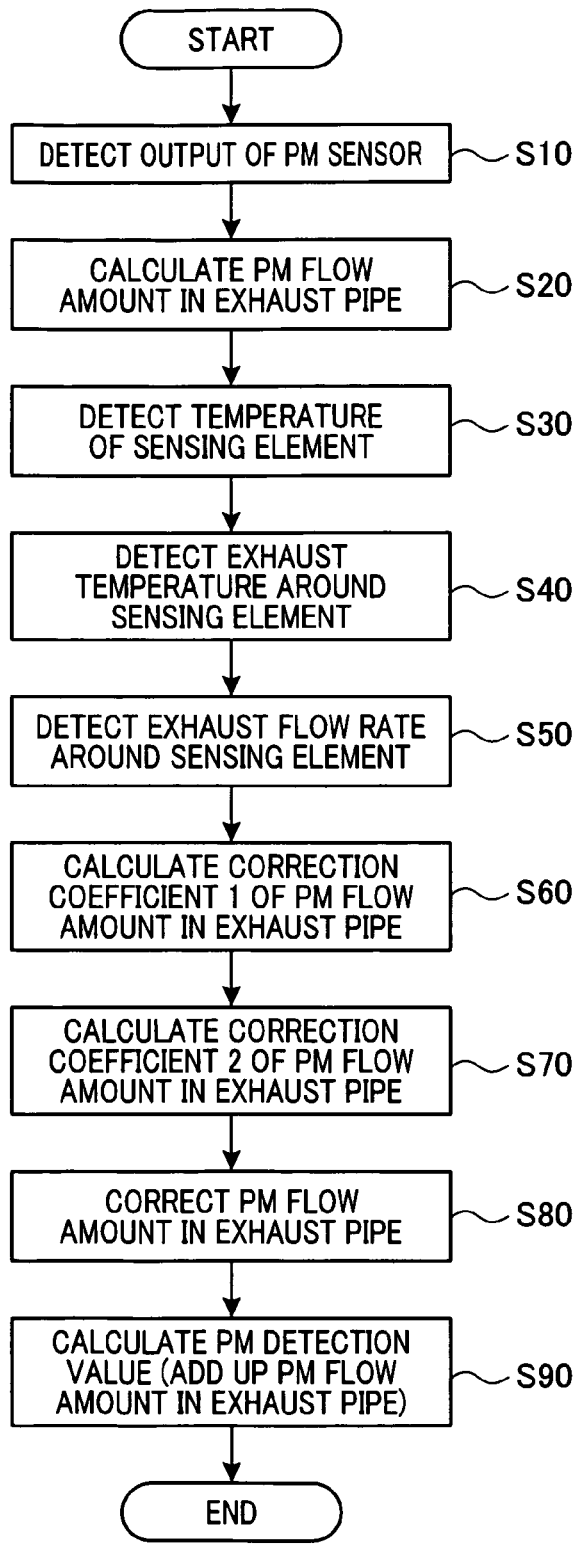
FIG. 5 is a flow diagram illustrating a process performed by a detection apparatus according to a second embodiment of the present invention.
Figure 8:
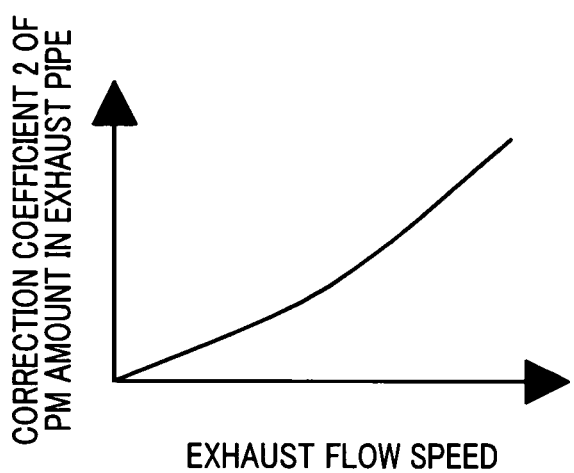
FIG. 8 is a graph illustrating correlation of correction coefficient for PM flow amount in an exhaust pipe, relative to exhaust flow rate, according to the second embodiment.

Referring now to FIGS. 5 and 8, hereinafter is described a second embodiment of the present invention. In the first embodiment described above, a PM flow amount in the exhaust pipe 4 has been corrected to eliminate the influence of thermal migration. In the second embodiment, a PM flow amount is corrected to eliminate the influence associated with exhaust flow speed, as well as the influence of thermal migration. The system configuration shown in FIGS. 1 to 3 may be used in the second embodiment.

FIG. 5 is a flow diagram illustrating a process performed by a detection apparatus according to the second embodiment. It should be appreciated that, in the second and the subsequent embodiments, the processing steps and the components identical with or similar to those of the first embodiment are given the same reference numerals for the sake of omitting unnecessary explanation.

In the process shown in FIG. 5, steps S50 and S70 are performed in addition to the steps of the first embodiment. At step S50, an exhaust flow speed around the sensing element 50 is detected. The process of calculating the exhaust speed will be described later. At step S70, the ECU 6 calculates a correction coefficient 2 (hereinafter also referred to as "coefficient 2") for the PM flow amount in the exhaust pipe 4. The coefficient 2 is used for eliminating the influence associated with the exhaust flow speed described above. For example, the coefficient 2 may be calculated using a map, an example of which is shown in FIG. 8. The map is prepared in advance in the ECU 6 (e.g., the memory 60).

In FIG. 8, the vertical axis indicates the correction coefficient 2 and the horizontal axis indicates exhaust flow rate (exhaust flow speed) per unit time. As mentioned above, as the exhaust flow speed becomes higher, the increase in the output of the PM sensor 5 for the PM flow amount in the exhaust pipe 4 becomes smaller. Thus, as the exhaust flow speed becomes higher, the coefficient 2 is set to a larger value. The vertical and horizontal axes of FIG. 8 are calibrated as appropriate according to the characteristics of the system to be used.

As described above, as the exhaust flow speed becomes higher, PM has a higher tendency of not being deposited on the sensing element 50 but of being separated from the sensing element 50. In order to compensate for this tendency, the curve plotted in the graph of FIG. 8 for determining the coefficient 2 is protruded downward. In other words, as the exhaust flow speed becomes higher, the increase rate (the inclination of the curve) of the coefficient 2 is rendered to be higher (steeper). At step S60, the coefficient 2 is calculated referring to the map shown in the graph of FIG. 8.

Then, at step S90 of FIG. 5, the PM flow amount in the exhaust pipe 4 acquired at step 20 is multiplied by the coefficient 1 calculated at step S60, followed by further multiplying the resultant value by the coefficient 2 calculated at step S70. Further, at step S100, the corrected PM flow amount in the exhaust pipe 4 is added up to calculate a PM detection value. The process shown in FIG. 5 is performed in this way.

(Third Embodiment)

Figure 6:
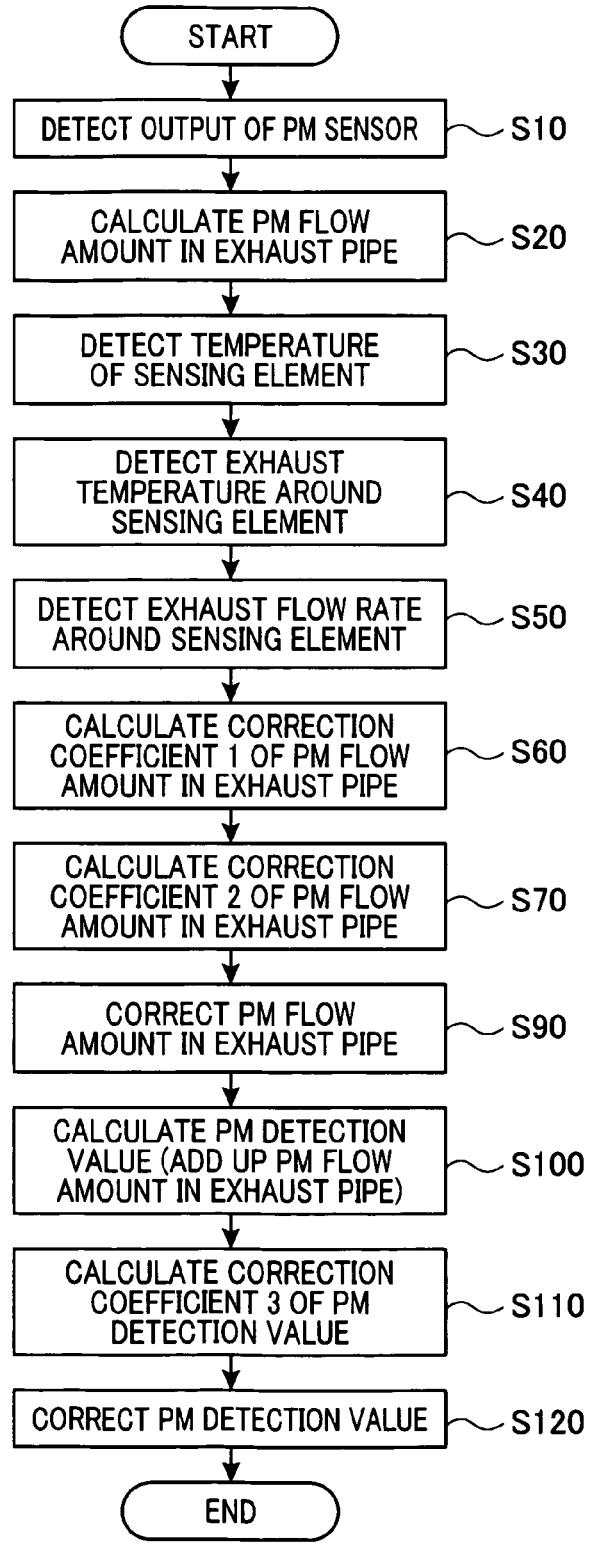
FIG. 6 is a flow diagram illustrating a process performed by a detection apparatus according to a third embodiment of the present invention.
Figure 9:
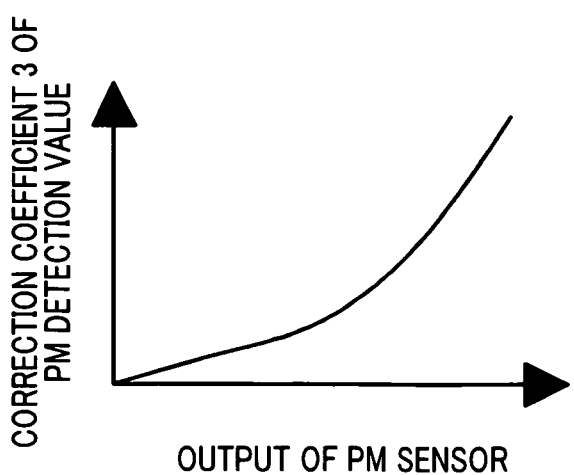
FIG. 9 is a graph illustrating a correlation of correction coefficient for PM flow amount in an exhaust pipe, relative to output of PM sensor, according to the third embodiment.

Referring to FIGS. 6 and 9, hereinafter is described a third embodiment of the present invention. In the third embodiment, a PM detection value is corrected to eliminate the influence of separation of the PM deposited on the sensing element 50, as well as the influence of thermal migration and the influence associated with exhaust flow speed. The system configuration shown in FIGS. 1 to 3 may be used in the present embodiment as well. FIG. 6 is a flow diagram illustrating a process performed by a detection apparatus according to the third embodiment. In the process shown in FIG. 6, steps S110 and S120 are performed in addition to the steps performed in the second embodiment. At step S110, the ECU 6 calculates a correction coefficient for a PM detection value (hereinafter also referred to as "coefficient 3"). The correction coefficient 3 is used for eliminating the influence of separation of the PM that has been accumulated on the surface of the sensing element 50 due to the influence associated with exhaust flow speed.

As the output of the PM sensor 5 becomes larger, more PM may be accumulated on the surface of the sensing element 50. Also, as more PM is accumulated on the sensing element 50, the amount of PM separating from the accumulation may be increased. Accordingly, as the output of the PM sensor 5 becomes larger, the amount of PM separating from the accumulation may be increased. Therefore, the influence of the correlation is corrected using the coefficient 3. For example, the coefficient 3 may be calculated using a map which uses the characteristics shown in the graph of FIG. 9. The map is prepared in advance in the ECU 6 (e.g., the memory 60). In other words, for the reasons mentioned above, as the output of the PM sensor 5 becomes larger, the value of the coefficient 3 is set to a larger value.

At step S110 of FIG. 6, the correction coefficient 3 is calculated referring to the map shown in the graph of FIG. 9. Then, at step S120 of FIG. 6, the PM detection value acquired at step S100 is multiplied by the coefficient 3 calculated at step S110 to obtain a corrected PM detection value.

Hereinafter is described the process of calculating an exhaust flow speed around the sensing element 50, which is used in the above embodiment. For example, an exhaust flow speed may be calculated by multiplying a volume flow rate per unit time in the exhaust pipe 4 (volume flow rate of the exhaust gas flowing through the exhaust pipe 4) by a coefficient. In the calculation of the volume flow rate, a mass flow rate per unit time of intake air measured by the air flow meter 30 is converted into a volume flow rate of the exhaust gas. For example, the volume flow rate is calculated using the following Formula (E1).

$$V(m^3/sec)=[[G(g/sec)/28.8(g/mol)]\times 22.4\times 10^{-3}(m^3/mol)+[Q(cc/sec)/207.3(g/mol)\times 0.84(g/cc)\times 6.75]\times 22.4\times 10^{-3}(m^3/mol)]\times [Teg(K)/273(K)]\times [P0(kPa)/[P0(kPa)+dP(kPa)]] \quad (E1)$$

In Formula (E1), "V (m³/sec)" indicates a volume flow rate of the exhaust gas flowing through the exhaust pipe 4, "G (g/sec)" indicates a mass flow rate per unit time of intake air, "Teg (K)" indicates an exhaust temperature, "dP (kPa)" indicates a pressure difference across the DPF and "Q (cc/sec)" indicates a fuel injection quantity per unit time. Further, the measurement values of the air flow meter 30 and the exhaust temperature sensor 40 may be used for "G" and "Teg", respectively. A command value for the quantity of injection toward an injector may be used for "Q".

In the right-hand side of Formula (E1), the first term indicates a mass flow rate of intake air converted into a volume flow rate. The second term indicates an increase that is a difference in the amount between the intake air and the exhaust gas after combustion of the injected fuel. In the second term, "0.84 (g/cc)" indicates a typical liquid density of light oil. The numeral "22.4×10⁻³ (m³/mol)" indicates a volume per 1 mol of an ideal gas at 0 degree centigrade and 1 atmosphere. Also, the numeral "6.75" indicates an increase rate in molar number of the exhaust gas for a fuel injection quantity of 1 mol.

The increase rate (6.75) is obtained as follows. Specifically, the composition of light oil is typically expressed by $C_{15}H_{27.3}$ (molecular weight: 207.3), and thus combustion is expressed by the following Reaction Formula (E2).

$$C_{15}H_{27.3}+21.75O_2 \rightarrow 15CO_2+13.5H_2O \qquad (E2)$$

Accordingly, the exhaust gas has a molar number which is 6.75 (=(15+13.5)−21.75) times larger than the fuel injection quantity of 1 mol.

Fuel is injected with injection intervals predetermined by the ECU 6 to achieve intermittent injection. The fuel injection quantity "Q" in Formula (E1) indicates an average fuel injection quantity taking into account not only the injecting period but also the non-injecting period.

The mass flow rate "G (g/sec)" per unit time of intake air may be measured by the air flow meter 30. The exhaust temperature "Teg (K)" may be measured by the exhaust temperature sensor 40. A command value for an injection quantity issued from the ECU 6 may be used for the fuel injection quantity "Q (cc/sec)" per unit time.

The volume flow rate of the exhaust gas flowing through the exhaust pipe 4 may be calculated by the following Formula (E3).

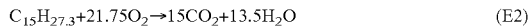

$$V(m^3/sec)=[[G(g/sec)/28.8(g/mol)]\times 22.4\times 10^{-3}(m^3/mol)+[Q(cc/sec)/207.3(g/mol)\times 0.84(g/cc)\times 6.75]\times 22.4\times 10^{-3}(m^3/mol)]\times [Teg(K)/273(K)]\times [P0(kPa)/[P0(kPa)\div dP(kPa)]] \qquad (E3)$$

The volume flow rate calculated by Formula (E3) corresponds to the exhaust flow speed at the upstream of the DPF 41. In Formula (E3), "P0 (kPa)" indicates an atmospheric pressure and "dP (kPa)" indicates a DPF pressure difference. For example, the DPF pressure difference may be measured by providing the DPF 41 with a differential-pressure meter.

The embodiments described above may be modified as appropriate within a scope not departing from the spirit of the invention. For example, the PM sensor 5 used in the above embodiments may be replaced by a PM sensor having a shunt resistor and for outputting a voltage. Any sensor may be used, if the sensor is able to output a value correlated to the PM amount in an exhaust pipe.

In the embodiments described above, the PM sensor 5 configures the particulate matter detection unit, and the ammeter 55 configures the detector of the particulate matter detection unit. The ECU 6, which performs processes in steps S30 and S40, the exhaust temperature sensor 40, and the heater controller 57 configure the temperature detection unit. The ECU 6, which includes the memory 60 and performs processes in steps S60-S120, configures the correction unit. The ECU 6 performs processes in steps S60 and S90, and configures the first sub-correction unit of the correction unit. The ECU 6 additionally configures the second sub-correction unit of the correction unit. The ECU 6 also configures the third sub-correction unit of the correction unit.

The ECU 6 also performs processes in steps S110 and S120, and configures the fourth sub-correction unit of the correction unit. The exhaust temperature sensor 40 configures the temperature sensor of the temperature detection unit. The ECU 6, which performs processes in step S30, configures the calculation unit. The heater 56 configures the heating unit. The heater controller 57 configures the first detector. The ECU 6 also configures the second detector. The air flow meter 30 configures the intake-volume detection unit. The ECU 6 configures the instruction unit.

The temperature in the vicinities of the insulator 50 and the electrodes 51 and 52 is raised by the heater 56. Immediately after the deposited PM is burned and removed, the PM detection value calculated at step S100 is set to zero (0).

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A detection apparatus, comprising:
   a particulate matter detection unit that includes
      an insulator that is disposed in an exhaust path of an internal combustion engine through which an exhaust gas flows,
      a pair of electrodes that are arranged in contact with at least a part of the insulator, and
      a detector that detects a particulate matter detection value which is a value correlated to an amount of particulate matter in the exhaust gas, the particulate matter attaching to the insulator and enabling current to flow between the pair of electrodes while voltage is applied across the pair of electrodes;
   an exhaust temperature detection unit that detects an exhaust temperature of the exhaust gas passing through the particulate matter detection unit;
   an insulator temperature detection unit that detects an insulator temperature of the insulator; and
   a correction unit that corrects the particulate matter detection value detected by the particulate matter detection unit based on the exhaust temperature detected by the exhaust temperature detection unit and the insulator temperature detected by the insulator temperature detection unit.

2. The detection apparatus according to claim 1, further comprising
   an exhaust flow rate detection unit that detects an exhaust flow rate of the exhaust gas passing through the insulator,
   wherein the correction unit corrects the particulate matter detection value detected by the particulate matter detection unit based on the exhaust flow rate detected by the exhaust flow rate detection unit and the exhaust temperature detected by the exhaust temperature detection unit and the insulator temperature detected by the insulator temperature detection unit.

3. The detection apparatus according to claim 2, further comprising
   a separation rate detection unit that detects a separation rate of particulate matter that separates from the insulator to which particulate matter is attached,
   wherein the correction unit corrects the particulate matter detection value detected by the particulate matter detection unit based on the separation rate of particulate matter detected by the separation rate detection unit, the exhaust flow rate detected by the exhaust flow rate detection unit, and the exhaust temperature detected by the exhaust temperature detection unit and the insulator temperature detected by the insulator temperature detection unit.

4. The detection apparatus according to claim 3, wherein
the separation rate detection includes an exhaust flow rate detection unit that detects an exhaust flow rate of the exhaust gas passing through the insulator, and a calculation unit that calculates the separation rate of particulate matter based on the particulate matter detection value and the exhaust flow rate.

5. The detection apparatus according to claim 1, wherein
the correction unit includes a first sub-correction unit that corrects a rate of change of the particulate matter detection value detected by the particulate matter detection unit in such a manner that, as a value obtained by subtracting the exhaust temperature from the insulator temperature becomes larger, the rate of change of the particulate matter detection value is corrected to a value indicating a larger amount of particulate matter.

6. The detection apparatus according to claim 5, wherein
the correction unit includes a second sub-correction unit that corrects the particulate matter detection value detected by the particulate matter detection unit in such a manner that, as the exhaust temperature or the insulator temperature becomes higher, the particulate matter detection value is corrected to a value indicating a larger amount of particulate matter.

7. The detection apparatus according to claim 6, further comprising
an exhaust flow rate detection unit that detects an exhaust flow rate of the exhaust gas passing through the insulator,
wherein the correction unit includes a third sub-correction unit that corrects a rate of change of the particulate matter detection value detected by the particulate matter detection unit in such a manner that, as the exhaust flow rate detected by the exhaust flow rate detection unit becomes larger, the rate of change of the particulate matter detection value is corrected to a value indicating a larger amount of particulate matter.

8. The detection apparatus according to claim 7, further comprising
a separation rate detection unit that detects a separation rate of particulate matter that separates from the insulator to which particulate matter is attached,
wherein the correction unit includes a fourth sub-correction unit that corrects the particulate matter detection value detected by the particulate matter detection unit in such a manner that, as the separation rate of particulate matter detected by the separation rate detection unit becomes larger, the particulate matter detection value is corrected to a value indicating a larger amount of particulate matter.

9. The detection apparatus according to claim 8, wherein
the fourth sub-correction unit corrects the particulate matter detection value detected by the particulate matter detection unit in such a manner that, as an output value of the particulate matter detection unit becomes larger, the particulate matter detection value is corrected to a value indicating a larger amount of particulate matter.

10. The detection apparatus according to claim 1, further comprising
an exhaust flow rate detection unit that detects an exhaust flow rate of the exhaust gas passing through the insulator,
wherein the exhaust temperature detection unit includes a temperature sensor that is disposed in the exhaust path and measures the exhaust temperature of the exhaust gas flowing in the exhaust path, and a calculation unit that calculates the exhaust temperature of the exhaust gas passing through the particulate matter detection unit based on the exhaust temperature measured by the temperature sensor and the insulator temperature detected by the insulator temperature detection unit and the exhaust flow rate of the exhaust gas detected by the exhaust flow rate detection unit.

11. The detection apparatus according to claim 1, further comprising
a heating unit that includes a resistor and a power unit that supplies the electric power to the resistor to heat the insulator,
wherein the insulator temperature detection unit includes a first detection unit that detects the insulator temperature based on a resistance value of the resistor.

12. The detection apparatus according to claim 1, further comprising:
a temperature sensor that that is disposed in the exhaust path and measures the exhaust temperature of the exhaust gas flowing in the exhaust path, and
an exhaust flow rate detection unit that detects an exhaust flow rate of the exhaust gas passing through the insulator, wherein
the insulator temperature detection unit detects the insulator temperature based on the exhaust temperature measured by the temperature sensor and the exhaust flow rate detected by the exhaust flow rate detection unit.

13. The detection apparatus according to claim 1, further comprising:
an exhaust flow rate detection unit that detects an exhaust flow rate of the exhaust gas passing through the insulator;
at least one of an instruction unit that instructs a fuel injection quantity for a cylinder of the internal combustion engine, a temperature sensor that that is disposed in the exhaust path and measures the exhaust temperature of the exhaust gas flowing in the exhaust path, and a pressure detection unit that detects an exhaust path pressure in the exhaust path of the internal combustion engine; and
an intake volume detection unit that detects an intake volume of an intake gas flowing in an intake path of the internal combustion engine,
wherein the exhaust flow rate detection unit detects the exhaust flow rate based on the intake volume detected by the intake volume detection unit and at least one of the fuel injection quantity instructed by the instruction unit, the exhaust temperature measured by the temperature sensor, and the exhaust path pressure detected by the pressure detection unit.

14. An engine system, comprising:
an internal combustion engine; and
a detection apparatus including
a particulate matter detection unit that includes
an insulator that is disposed in an exhaust path of the internal combustion engine through which an exhaust gas flows,
a pair of electrodes that are arranged in contact with at least a part of the insulator, and
a detector that detects a particulate matter detection value which is a value correlated to the amount of particulate matter in the exhaust gas, the particulate matter attaching to the insulator and enabling current to flow between the pair of electrodes while voltage is applied across the pair of electrodes;
an exhaust temperature detection unit that detects an exhaust temperature of the exhaust gas passing through the particulate matter detection unit;

an insulator temperature detection unit that detects an insulator temperature of the insulator; and
a correction unit that corrects the particulate matter detection value detected by the particulate matter detection unit based on the exhaust temperature detected by the exhaust temperature detection unit and the insulator temperature detected by the insulator temperature detection unit.

15. The engine system according to claim 14, further comprising
a particulate filter that is disposed in the exhaust path and collects particulate matter in the exhaust gas of the internal combustion engine.

16. The engine system according to claim 15, wherein
the internal combustion engine is a diesel engine, and
the particulate filter is a diesel particulate filter for the diesel engine.

17. The engine system according to claim 14, wherein:
the detection apparatus further comprises an exhaust flow rate detection unit that detects an exhaust flow rate of the exhaust gas passing through the insulator,
wherein the correction unit corrects the particulate matter detection value detected by the particulate matter detection unit based on the exhaust flow rate detected by the exhaust flow rate detection unit and the exhaust temperature detected by the exhaust temperature detection unit and the insulator temperature detected by the insulator temperature detection unit.

18. The engine system according to claim 14, wherein
the correction unit includes a first sub-correction unit that corrects a rate of change of the particulate matter detection value detected by the particulate matter detection unit in such a manner that, as a value obtained by subtracting the exhaust temperature from the insulator temperature becomes larger, the rate of change of the particulate matter detection value is corrected to a value indicating a larger amount of particulate matter.

19. A detection method, comprising:
(i) at a particulate matter detection unit including an insulator that is disposed in an exhaust path of an internal combustion engine through which an exhaust gas flows, a pair of electrodes that are arranged in contact with at least a part of the insulator, and a detector, detecting a particulate matter detection value which is a value correlated to an amount of particulate matter in the exhaust gas, the particulate matter attaching to the insulator and enabling current to flow between the pair of electrodes while voltage is applied across the pair of electrodes;
(ii) at an exhaust temperature detection unit, detecting an exhaust temperature of the exhaust gas passing through the particulate matter detection unit;
(iii) at an insulator temperature detection unit, detecting an insulator temperature of the insulator; and
(iv) at a correction unit, correcting the particulate matter detection value detected by the particulate matter detection unit based on the exhaust temperature detected by the exhaust temperature detection unit and the insulator temperature detected by the insulator temperature detection unit.

20. The detection method according to claim 19, further comprising
(v) at an exhaust flow rate detection unit, detecting an exhaust flow rate of the exhaust gas passing through the insulator,
wherein the correction unit corrects the particulate matter detection value detected by the particulate matter detection unit based on the exhaust flow rate detected by the exhaust flow rate detection unit and the exhaust temperature detected by the exhaust temperature detection unit and the insulator temperature detected by the insulator temperature detection unit.

21. The detection method according to claim 20, further comprising
(vi) at a separation rate detection unit, detecting a separation rate of particulate matter that separates from the insulator to which particulate matter is attached,
wherein the correction unit corrects the particulate matter detection value detected by the particulate matter detection unit based on the separation rate of particulate matter detected by the separation rate detection unit, the exhaust flow rate detected by the exhaust flow rate detection unit, and the exhaust temperature detected by the exhaust temperature detection unit and the insulator temperature detected by the insulator temperature detection unit.

* * * * *